US005968013A

United States Patent [19]
Smith et al.

[11] Patent Number: 5,968,013
[45] Date of Patent: Oct. 19, 1999

[54] MULTI-FUNCTION DILATATION CATHETER

[75] Inventors: Scott R. Smith, Chaska; David J. Sogard, Edina, both of Minn.

[73] Assignee: SciMed Life Systems, Inc., Maple Grove, Minn.

[21] Appl. No.: 08/915,887

[22] Filed: Aug. 21, 1997

[51] Int. Cl.$^6$ ................................................ A61M 29/00
[52] U.S. Cl. ........................... 604/102; 604/96; 604/103; 606/159
[58] Field of Search ...................... 604/96–103; 606/192, 606/194, 159

[56] References Cited

U.S. PATENT DOCUMENTS

| | | | |
|---|---|---|---|
| 3,585,983 | 6/1971 | Kastrowitz et al. | 128/1 |
| 3,834,394 | 9/1974 | Hunter et al. | 128/325 |
| 4,276,874 | 7/1981 | Wolvek et al. | 128/1 |
| 4,362,150 | 12/1982 | Lombardi, Jr. et al. | 128/1 |
| 4,402,307 | 9/1983 | Hanson et al. | 128/1 |
| 4,444,186 | 4/1984 | Wolvek et al. | 128/325 |
| 4,581,017 | 4/1986 | Sahota | 604/101 |
| 4,646,719 | 3/1987 | Neuman et al. | 128/1 |
| 4,689,041 | 8/1987 | Corday et al. | 604/53 |
| 4,771,777 | 9/1988 | Horzewski et al. | 128/344 |
| 4,790,315 | 12/1988 | Mueller, Jr. et al. | 128/344 |
| 4,820,349 | 4/1989 | Saab | 128/344 |
| 4,877,031 | 10/1989 | Conway et al. | 128/344 |
| 4,892,519 | 1/1990 | Songer et al. | 604/96 |
| 4,921,483 | 5/1990 | Wijay et al. | 604/96 |
| 4,944,745 | 7/1990 | Sogard et al. | 606/194 |
| 5,000,734 | 3/1991 | Boussignac et al. | 604/96 |
| 5,046,503 | 9/1991 | Schneiderman | 128/692 |
| 5,057,120 | 10/1991 | Farcot | 606/194 |
| 5,087,247 | 2/1992 | Horn et al. | 604/98 |
| 5,090,958 | 2/1992 | Sahota | 604/98 |
| 5,114,423 | 5/1992 | Kasprzyk et al. | 606/27 |
| 5,158,540 | 10/1992 | Wijay et al. | 604/43 |
| 5,160,321 | 11/1992 | Sahota | 604/96 |
| 5,195,971 | 3/1993 | Sirhan | 604/96 |
| 5,201,723 | 4/1993 | Quinn | 604/264 |
| 5,257,974 | 11/1993 | Cox | 604/96 |
| 5,279,562 | 1/1994 | Sirhan et al. | 604/96 |
| 5,295,962 | 3/1994 | Crocker et al. | 604/101 |
| 5,300,085 | 4/1994 | Yock | 606/191 |
| 5,338,300 | 8/1994 | Cox | 604/96 |
| 5,368,566 | 11/1994 | Crocker | 604/101 |
| 5,378,237 | 1/1995 | Boussignac et al. | 604/96 |
| 5,383,890 | 1/1995 | Miraki et al. | 606/194 |
| 5,522,800 | 6/1996 | Crocker | 604/96 |
| 5,542,925 | 8/1996 | Orth | 604/102 |
| 5,542,926 | 8/1996 | Crocker | 604/102 |

FOREIGN PATENT DOCUMENTS

| | | |
|---|---|---|
| 0 246 998 A2 | 11/1987 | European Pat. Off. . |
| 0 353 889 A1 | 2/1990 | European Pat. Off. . |
| 0 441 384 A2 | 8/1991 | European Pat. Off. . |
| 0 517 654 A2 | 12/1992 | European Pat. Off. . |
| 0 629 417 A2 | 12/1994 | European Pat. Off. . |
| WO 92/20398 | 11/1992 | WIPO . |

Primary Examiner—Wynn Wood Coggins
Assistant Examiner—Deborah Blyveis
Attorney, Agent, or Firm—Crompton, Seager & Tufte, LLC

[57] ABSTRACT

An improved multi-function catheter structure having an inflatable balloon structure at its distal end, to selectively occlude a vascular lumen, provide antegrade perfusion liquid distally of the inflatable balloon, and provide retrograde perfusion proximally of the inflatable balloon is described.

30 Claims, 6 Drawing Sheets

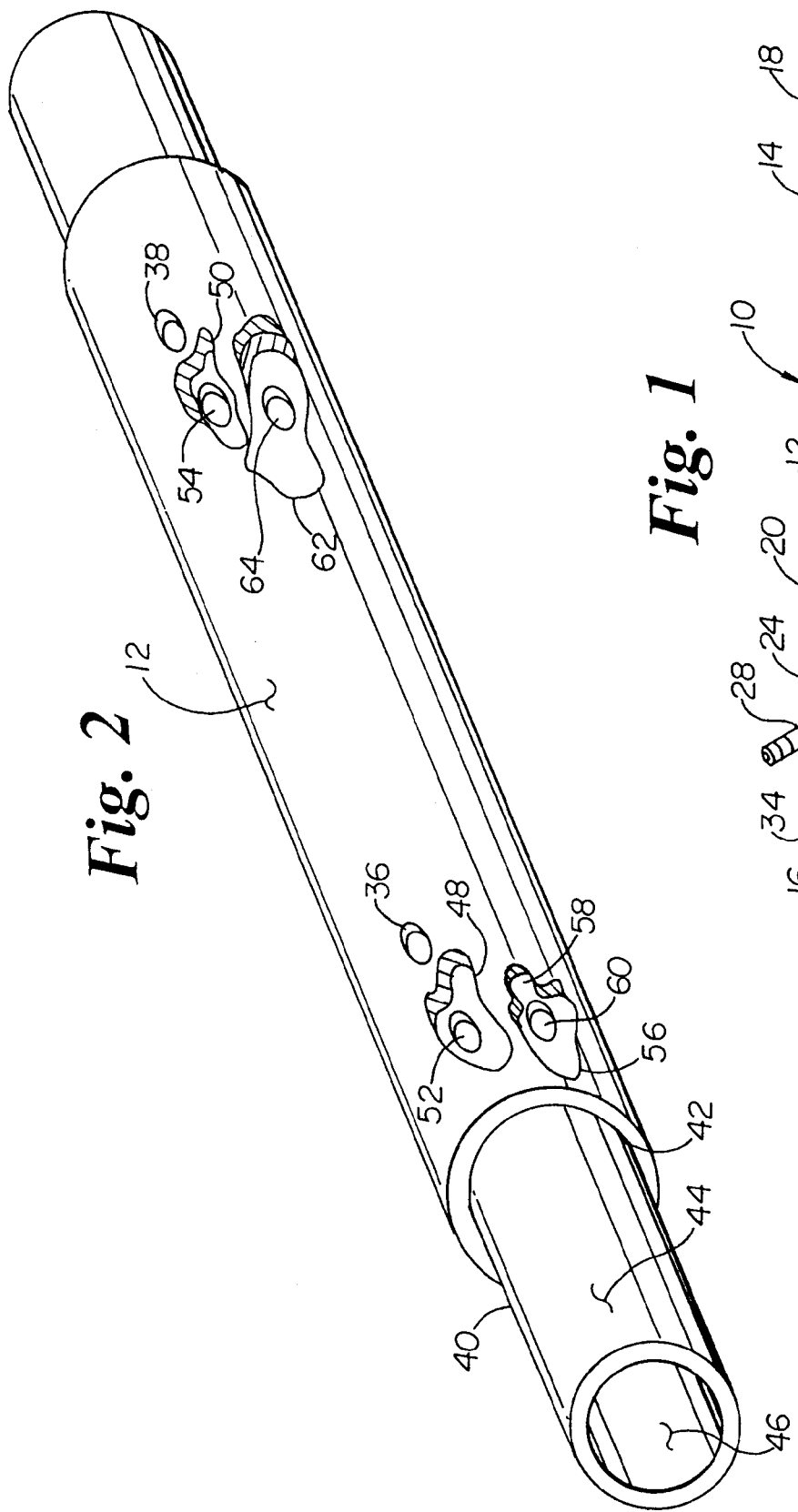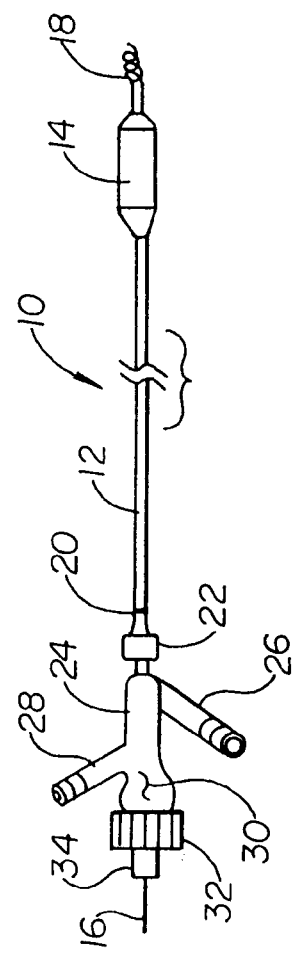

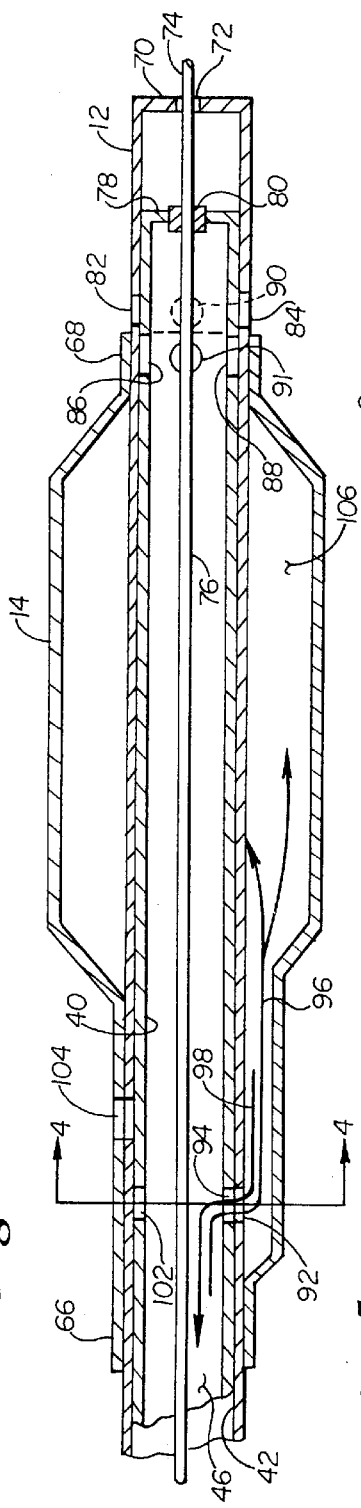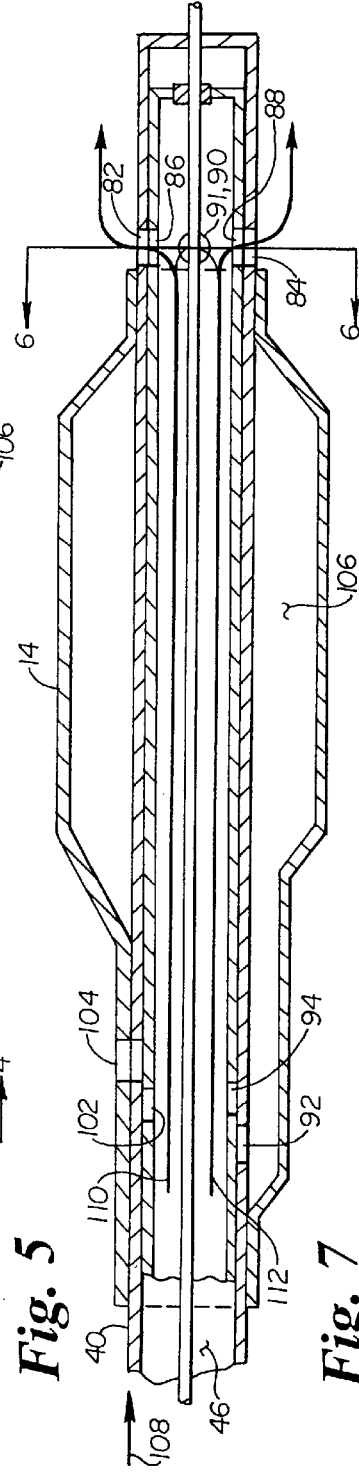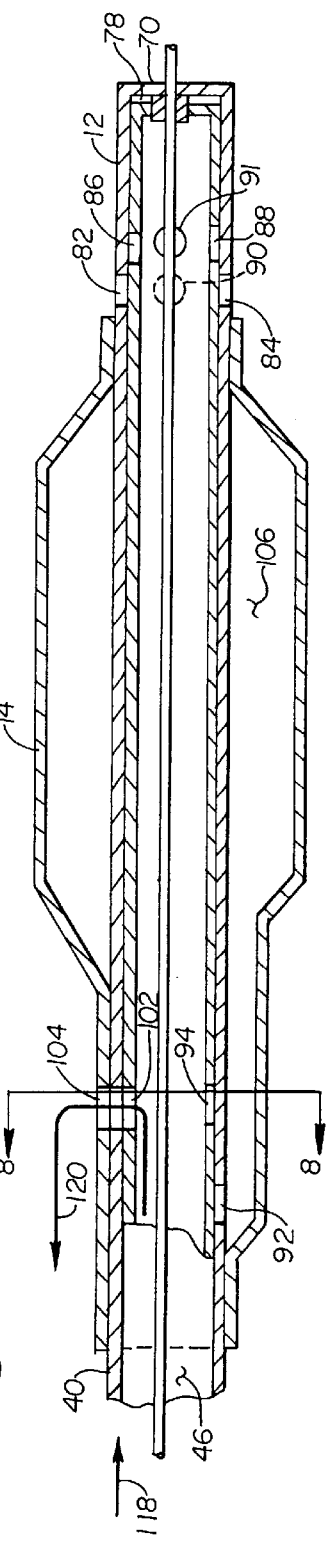
Fig. 3
Fig. 5
Fig. 7

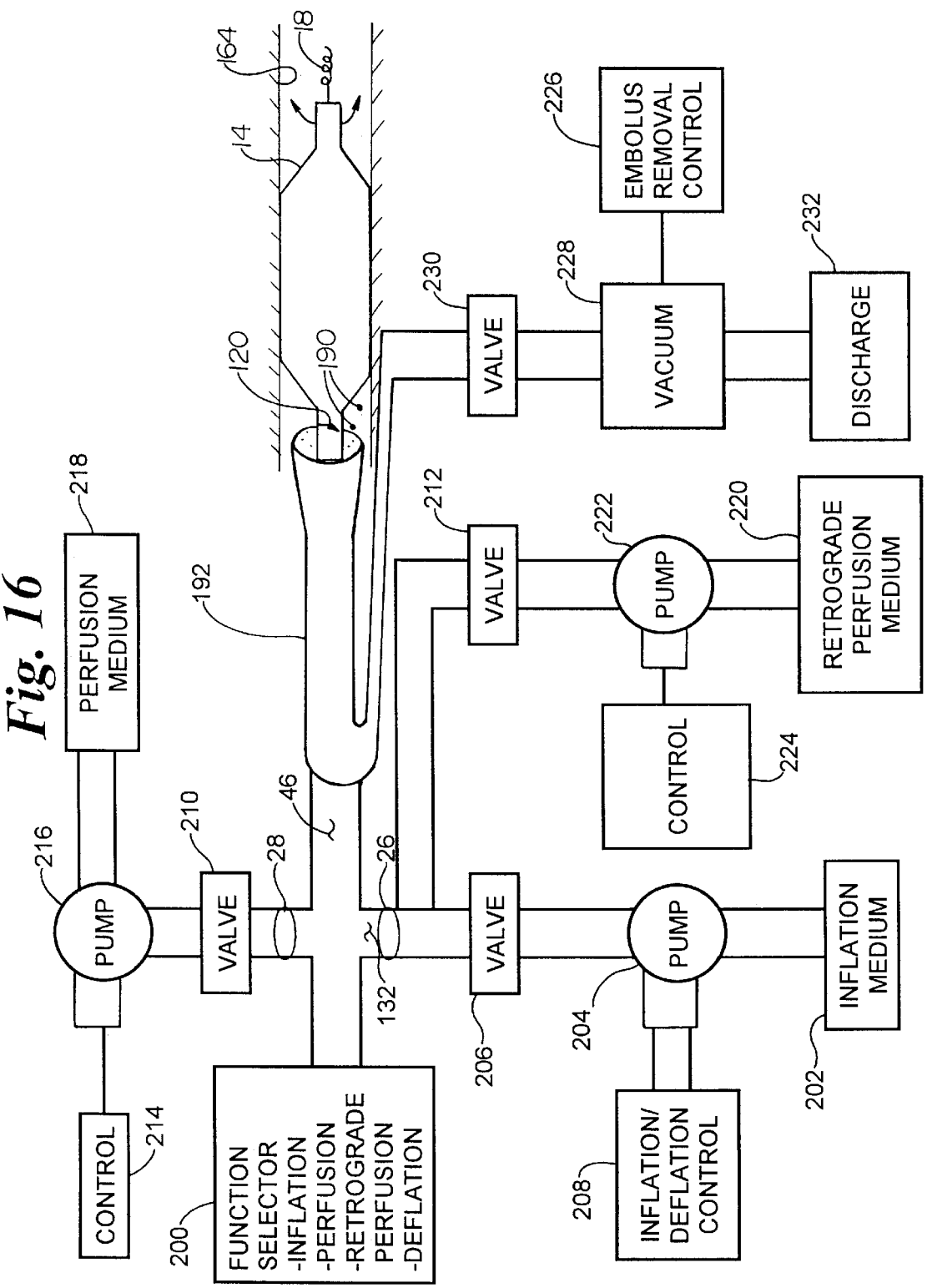

MULTI-FUNCTION DILATATION CATHETER

BACKGROUND OF THE INVENTION

1. Technical Field of the Invention

The present invention relates generally to a dilatation catheter used in angioplasty; and, more particularly, it relates to a dilatation catheter suitable for percutaneous transluminal angioplasty procedures which can perfuse blood distally of a dilatation occluding device, provide treatment of stenosis, and removal of resulting embolus.

2. State of the Prior Art

A stenosis is a narrowing or constriction of a region of a blood vessel to such a degree that blood flow is restricted. Such restrictions can be caused by a variety of restrictions, including existence of thrombus, blood clotting or deposits of cholesterol crystals, calcium, plaque, or the like. If the stenotic condition is sufficiently severe, medical treatment is required to restore adequate blood flow. These conditions can require treatment ranging from surgery under general anaesthetic for the most severe cases to angioplasty using a local anaesthetic for less severe stenotic conditions.

It is known that stenosis can occur in the arteries and, especially, the coronary arteries. In the coronary arteries, stenosis is treated by a Percutaneous Transluminal Coronary Angioplasty procedure, commonly known as PTCA, which involves percutaneous insertion of a balloon catheter to the point of stenosis. The precise point of treatment will be determined by the nature of the procedure that will be utilized. When properly located, a fluid is inserted into the balloon to cause it to expand outwardly. When placed at the point of the stenosis, the expansion outwardly under pressure causes the stenosis to be compressed against the artery wall to thereby open the artery for improved blood flow.

Many prior art balloon catheters have the disadvantages of occluding blood flow while the balloon is expanded. A number of patents describe balloon catheter structures for directly treating stenosis in this manner. Such prior art devices are not without deficiencies in the efficacy of the treatment procedure of only applying pressure to the stenosis. Blood flow stoppage for a relatively short period of time can cause damage to the portion of the vascular system or part of the heart to which the flow of blood is interrupted. An ancillary problem relates to the amount of expansion of the balloon. If expanded too far, the artery can be ruptured. Finally, while the stenosis has been compressed by the balloon, a relaxation of pressure can allow particles of the stenosis to be detached or flaked off to become free particles or embolus in the blood. If left unrecovered, such embolus can cause damage to the heart or vascular system as the embolus circulates.

A number of prior art patents have described structures to perfuse blood flow through an expanded balloon to treat stenosis. These structures allow the balloon to be expanded longer to treat the stenosis while allowing blood to flow past the occlusion. Some examples of perfusion dilatation catheters are shown in U.S. Pat. Nos. 4,581,017 to Sahota, where blood in the artery is perfused through apertures proximally and distally of the balloon; 5,279,562 to Sirhan et al., where arterial blood is perfused through a special structure to a point distal of a balloon; 5,368,566 to Crocker, where arterial blood is perfused through a reinforced structure; 4,892,519 to Songer et al., where arterial blood is perfused through proximal apertures to an interior lumen for passing through an inflatable balloon to distal apertures; 4,944,745 to Sogard et al., where arterial blood flow through a special lumen through an inflated lumen balloon to a distal port; and 5,542,925 to Orth, where arterial blood passes through specially shaped proximal ports into an interior lumen for passing through an inflated balloon to distally located shaped ports. Prior art devices use relatively complex equipment and sequences of operation to minimize damage to the vascular lumen tissue, to the downstream portions of the vascular system, and of the patient's heart.

It has been shown that complete occlusion of a vascular lumen for more than a few seconds can cause such damage. The prior art has shown systems that provide distal perfusion to minimize such damage from occluding the vascular lumen, but they too are unduly complex and require multiple structures to achieve occlusion and related treatment procedures. Further, they suffer from the major defect that embolus occurring proximally of an inflated balloon may pass downstream in the perfused flow, thereby risking damage to the vascular system or heart. This risk should be avoided. These systems also rely on the pressure of the vascular system for perfusion, and such pressure may vary to a degree that adequate perfusion for the various systems that damage may occur.

SUMMARY OF THE INVENTION

The present invention provides an elongated catheter body having an outer surface with proximal and distal ends and an inner lumen with a plurality of apertures formed in the vicinity of the distal end, and an elongated outer body coaxially positioned along the elongated catheter body and in slidable engagement with the outer surface. The elongated outer body has a similar plurality of apertures that are arranged such that the positioning of the catheter within the outer body at different positions results in different combinations of apertures in the catheter and in the outer body being in cooperative fluid-flow positions. In this manner, a first position of the catheter relative to the outer body results in inflation fluid flow apertures being aligned such that an associated inflatable balloon can be inflated to occlude a vascular or coronary lumen, or can be utilized to apply pressure to stenotic material. When a second position of the catheter within the outer body is selected, antegrade perfusion flow apertures in the catheter and outer body will be in alignment for cooperation in fluid-flow to allow perfusion media applied through the catheter lumen to be injected in the vascular lumen distally of the inflatable balloon structure. Finally, when the catheter is positioned in a third position relative to the outer body, retrograde perfusion flow apertures of the plurality of apertures in the catheter and the outer body are brought into alignment for cooperation in fluid-flow to allow retrograde perfusion liquid applied in the lumen of the catheter to provide retrograde perfusion proximally of the inflated balloon structure.

The present invention is contemplated to be used in conjunction with devices for performing atherectomy procedures. It is also contemplated that the present invention may be used in other fields such as urology and gastroenterology.

The invention can provide a percutaneous catheter structure that can occlude a vascular lumen while allowing distal perfusion and can cooperate with a mechanism to remove stenotic material. In another aspect of the invention, then a steerable inflatable balloon catheter is percutaneously positioned such that an inflatable balloon structure is positioned distally of the stenosis. When the balloon structure is inflated and the perfusion flow established through the lumen of the catheter, an abrading mechanism is passed along the catheter structure to a position to allow the stenotic material to be removed or abraded in a predetermined manner. The removal process results in the formation of embolus. Upon removal of the stenosis-removal mechanism from the area where the stenosis had existed, a removal catheter is placed in position near the proximal end of the inflatable balloon and retrograde perfusion fluid is passed through the lumen of the catheter proximally of the inflatable balloon. In this arrangement, when vacuum is applied to the removal catheter, embolus is withdrawn from the vascular lumen.

The invention can provide a multi-function catheter having an inflatable balloon structure at its distal end that can be percutaneously inserted and controlled in its multi-function operation externally. In another aspect of the invention, an external control mechanism is provided for controlling the relative longitudinal positioning of an elongated catheter and a coaxially positioned elongated outer body that is in slidable contact with the catheter. The elongated catheter and the outer body each have a plurality of apertures in the vicinity of their respective distal ends, such that the slidable, longitudinal positioning of the catheter relative to the outer body result in different ones of the plurality of apertures in the catheter and in the outer body to be brought into positions for fluid flow.

When the external control mechanism brings the catheter into a first position, inflation fluid can be passed through the lumen of the catheter and through aligned apertures in the catheter and the outer body to cause predetermined inflation of the an inflatable balloon. When the control mechanism brings the longitudinal alignment of the catheter and the outer body to a second position, antegrade perfusion fluid can pass through the lumen of the catheter, out through the outer body and into the lumen of the artery distally of the inflated balloon structure. When the catheter body is moved by the control mechanism into a third position relative to the outer body, other apertures in the catheter and the outer body are aligned, and retrograde perfusion fluid can be passed through the lumen of the catheter and outwardly through the catheter and the outer body via the aligned apertures proximally of the inflated balloon structure. The retrograde perfusion thereby urges embolus away from the balloon structure in a proximal direction.

In this manner, at different times, the lumen of the catheter serves as the carrier for the inflation fluid, the antegrade perfusion fluid and the retrograde perfusion fluid. Once the medical procedure has been completed, the catheter can be moved by the controlled mechanism to the first position and the inflation fluid can be drawn back from the inflated balloon through the lumen of the catheter such that the balloon structure is deflated and the entire structure can be removed.

The invention can provide an improved catheter structure that is multi-functional in providing inflation of an inflatable balloon, distal perfusion, and proximal retrograde perfusion utilizing a simple and economical catheter structure. An embodiment has been provided of an improved catheter wherein a single catheter when used in combination with an outer body can selectively carry in the lumen of the catheter the inflation fluid, the distal perfusion fluid, and the proximal retrograde perfusion fluid.

The invention can provide an improved catheter system having an inflatable balloon structure near its distal end that is maneuverable for selective location in vascular or coronary arteries. In one embodiment, a guidewire is utilized for initial positioning with the catheter when being moved along the guidewire to the location of the stenosis to be treated. In another embodiment, the catheter is fixed with a flexible tip and is established with a sufficiently flexible catheter and outer body structure such that the entire catheter structure is steerable and can be positioned to the area of the stenosis to be treated.

The invention can provide an improved catheter structure having an inflatable balloon structure near its distal end to provide an alternative to surgery for patient's having stenotic arteries. The invention achieves this objective by permitting percutaneous location of a catheter having an inflatable balloon structure that selectively allows application of perfusion fluids distally of the inflatable balloon structure during the process of removing the stenotic material from the walls of the artery, and thereafter allows the application of retrograde perfusion fluid through the catheter to assist in removal of the embolus.

The foregoing and other more detailed and specific objectives of the invention will become apparent from a consideration of the description of the preferred embodiment in reference to the drawings.

BRIEF DESCRIPTION OF THE DRAWINGS

FIG. 1 is a foreshortened view of the multi-function catheter structure of the invention;

FIG. 2 is a partial perspective view of coaxially arranged outer body and catheter structures that are slidably engaged;

FIG. 3 is a section view of the distal tip of a multi-function catheter illustrating inflation of a balloon structure;

FIG. 5 is a section view of the distal tip of a multi-function catheter illustrating perfusion in a vascular lumen occluded by an inflated balloon;

FIG. 7 is a section view of the distal tip of a multi-function catheter illustrating retrograde perfusion in a vascular lumen occluded by an inflated balloon;

FIG. 16 is a block diagram of the controls utilized to operate the multi-function catheter and balloon structure to perform the functions of occluding the artery, providing distal perfusion past the inflated balloon, and providing retrograde perfusion at the proximal end of the inflated balloon.

DETAILED DESCRIPTION OF THE PREFERRED EMBODIMENTS

Figure 4:
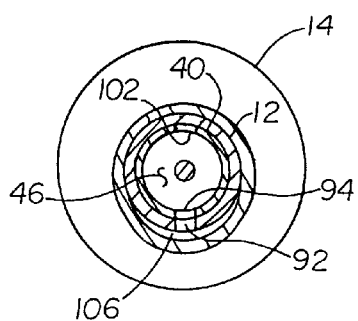
FIG. 4 is a cross-sectional view taken at line 4—4 in FIG. 3 and illustrates alignment of inflation apertures.

FIG. 1 is the foreshortened view of the multi-function catheter structure of the invention.

The multi-functional catheter 10 has an elongated outer member 12 with an inflatable balloon 14 at its distal end. A guidewire 16 passes the length of the multi-function catheter structure and terminates at a distal end 18. The distal end 18 can be formed as a helical coil to assist in guiding the multi-function catheter structure through a tortuous path in a vascular lumen. The proximal end 20 of member 12 is gripped by mounting member 22. A manifold structure 24 has a first threaded input tube 26 and a second threaded input tube 28. A control structure, to be described in more detail below, is enclosed in proximal portion 30 and is subject to positioned control through actuation of control knob 32. Control 34 is used for manipulating the guidewire 16. In operation, the distal tip 18 is inserted in a vascular lumen for percutaneous insertion of the inflatable balloon member 14 and the necessary length of elongated member 12 to reach the point where stenosis is to be treated or other medical treatment is to be done.

FIG. 2 is a partial perspective view of coaxially arranged outer body and catheter structures that are slidably engaged. As illustrated, outer body 12 has a first aperture 36 and a second aperture 38 through its thickness. A portion of the elongated catheter 40 is slidably engaged with the inner surface 42 of outer body member 12 and is coaxially arranged. In this configuration, apertures 36 and 38 are blocked by the outer surface 44 of catheter 40 from fluid communication with the lumen 46. Breakaway portion 48 and 50 expose apertures 52 and 54, respectively, through catheter 44. Without any aperture formed in outer body 12 in conjunction with apertures 52 and 54, fluid passing through lumen 46 would be prevented from passing outwardly through the outer body by the blocking action of outer body 12. At broken away portion 56, aperture 58 in outer body 12 is in fluid-flow alignment with aperture 60 through catheter 40. When thus aligned, fluid passed through lumen 46 would be in flow through apertures 58 and 60. In a similar manner, at breakaway portion 62, aperture 64 is in fluid-flow alignment with an aperture (not shown) broken away from outer body member 12. The specific configuration of apertures in outer body 12 and catheter structure 40 will be described for each of the functions of the multi-function catheter. The apertures can be shaped to achieve the desired type of fluid-flow. The number of cooperating apertures for each function can likewise be selected to achieve the type of fluid-flow required for each function.

In an alternate embodiment not shown, elongate catheter 40 can rotate coaxially relative to outer body member 12. In this configuration, rather than sliding elongate catheter 40 relative to outer body member 12 to align the various apertures, elongate catheter 40 is rotated relative to outer body member 12 to align the various apertures. The functions and effect of aligning the various apertures would be the same or similar to that described above.

In yet another embodiment, elongate catheter 40 would not extend the full length of outer body member 12. In such a case, a proximal portion of elongate catheter 40 could be replaced by a push/pull wire to enable the various aperture configurations. The use of the push/pull wire is believed to reduce the push/pull friction that would exist between full length elongate catheter 40 and outer body member 12. The cross section of the outer body member 12 could also be reduced in the region of the push/pull wire.

FIG. 3 is a section view of the distal tip of the multi-function catheter illustrating inflation of a balloon structure. In this configuration, inflatable balloon structure 14 is illustrated expanded and has a proximal end 66 at a distal end 68. The longitudinal outer body 12 extends through the inflatable balloon 14, and the proximal end 66 and distal end 68 are affixed or bonded to the outer surface of outer body 12. The elongated catheter structure 40 is in slidable contact with the inner surface 42 of outer member 12. The distal end 70 of outer member 12 has an aperture 72 through which the distal end 74 of guidewire 76 passes. The distal end 78 of catheter 40 has a mounting block 80 for slidably supporting guidewire 76. Near its distal end, outer body member 12 has apertures 82, 84 and 90. Near its distal end, catheter structure 40 has apertures 86, 88 and 91, which are positioned to cooperate to provide fluid-flow with apertures 82, 84 and 90, respectively, when properly positioned. Proximal of the balloon structure 14, outer body 12 has aperture 92 positioned for fluid-flow cooperation with aperture 94 in catheter 40. When thus positioned in a fluid-flow cooperative relationship, apertures 92 and 94 allow for passage of inflation fluid through lumen 46 in the direction of arrow 96 to cause inflation of balloon structure 14. As will be described in more detail below, when the medical procedures are completed and the multi-function catheter is to be removed, apertures 92 and 94 are again aligned and through a vacuum drawn in lumen 46, inflation fluid is drawn through apertures 92 and 94 in the direction of arrow 98 such that the balloon structure 14 collapses and disengages the inner surface of the vascular lumen with which it is associated.

Retrograde perfusion aperture 102 in catheter 40 and aperture 104 in outer member 12 are not in alignment and there is no fluid-flow therebetween.

FIG. 4 is a cross-sectional view taken at line 4—4 in FIG. 3 and illustrates alignment of the mating inflation apertures. As shown, lumen 46 of catheter 40 is in fluid-flow communication through apertures 94 and 92 to chamber 106 within inflatable balloon structure 14. This alignment allows insertion of inflation fluid into chamber 106 from lumen 46 for causing the balloon structure 14 to inflate.

FIG. 5 is a section view of the distal tip of a multi-function catheter illustrating perfusion in a vascular lumen occluded by an inflated balloon. In this configuration, it can be seen that catheter structure 40 has been moved in the direction of arrow 108 such that perfusion apertures 82 and 86 are aligned, apertures 84 and 88 are aligned, and aperture 91 is disposed over aperture 90. In this configuration, perfusion fluid can pass in the direction arrows 110 and 112 in lumen 46 to be passed out through the aligned perfusion apertures distally of the inflated balloon structure 14. In this position, inflation apertures 92 and 94 are misaligned such that inflation fluid retained in chamber 106 will cause balloon structure 14 to remain inflated. Further, retrograde perfusion apertures 102 and 104 are misaligned so that there is no escape of perfusion fluid proximally of balloon structure 14.

Figure 6:
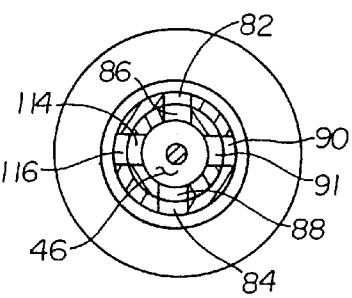
FIG. 6 is a cross-sectional view taken at line 6—6 in FIG. 5 and illustrates alignment of mating perfusion apertures.

FIG. 6 is a cross-sectional view taken at line 6—6 in FIG. 5 and illustrates alignment of mating perfusion apertures. As illustrated, in this configuration, apertures 82 and 86 are aligned, apertures 84 and 88 are aligned, apertures 90 and 91 are aligned and apertures 114 and 116 are aligned, thereby allowing antegrade perfusion fluid to flow from lumen 46 outwardly therethrough. It should be noted that the configuration of mating perfusion apertures may be fewer or greater in number than those shown, and may be staggered or otherwise differently aligned along the length of outer body 12 and catheter structure 14. The alignment, size of apertures and spacing, will be dependent upon the necessary flow of perfusion fluid therethrough in conjunction with the physical dimension of the structure and apertures.

FIG. 7 is a section view of a distal tip of a multi-function catheter illustrating retrograde perfusion in a vascular lumen occluded by an inflated balloon. In this configuration, lumen 40 is moved farther in the direction of arrow 118 such that its distal end 78 comes into close proximity with the distal end 70 of the outer member 12. In this arrangement, retrograde perfusion apertures 102 and 104 are aligned. When thus aligned, retrograde perfusion fluid flow can pass in the direction of arrow 120 outwardly through the aligned apertures 102 and 104 from lumen 46 in a location proximal of the inflated balloon 14. When thus positioned, inflation apertures 92 and 94 are misaligned so that inflation fluid in chamber 106 retains the inflated balloon structure 14 in an inflated state. The mating pairs perfusion apertures 82 and 86, 84 and 88, and 90 and 91 are misaligned so that there is no perfusion fluid flow at the distal end of the catheter structure during the functioning of the retrograde perfusion.

Figure 8:
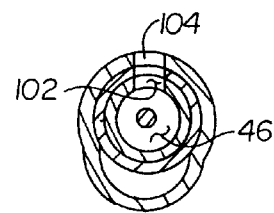
FIG. 8 is a cross-sectional view taken at line 8—8 in FIG. 7 and illustrates alignment of mating retrograde perfusion apertures.

FIG. 8 is a cross-sectional view taken at line 8—8 in FIG. 7 and illustrates alignment of mating retrograde perfusion apertures. As shown, mating apertures 102 and 104 are aligned and in fluid-flow communication with lumen 46. It is understood that additional pairs of mating apertures can be utilized to carry and pass additional retrograde perfusion fluid.

Figure 9:
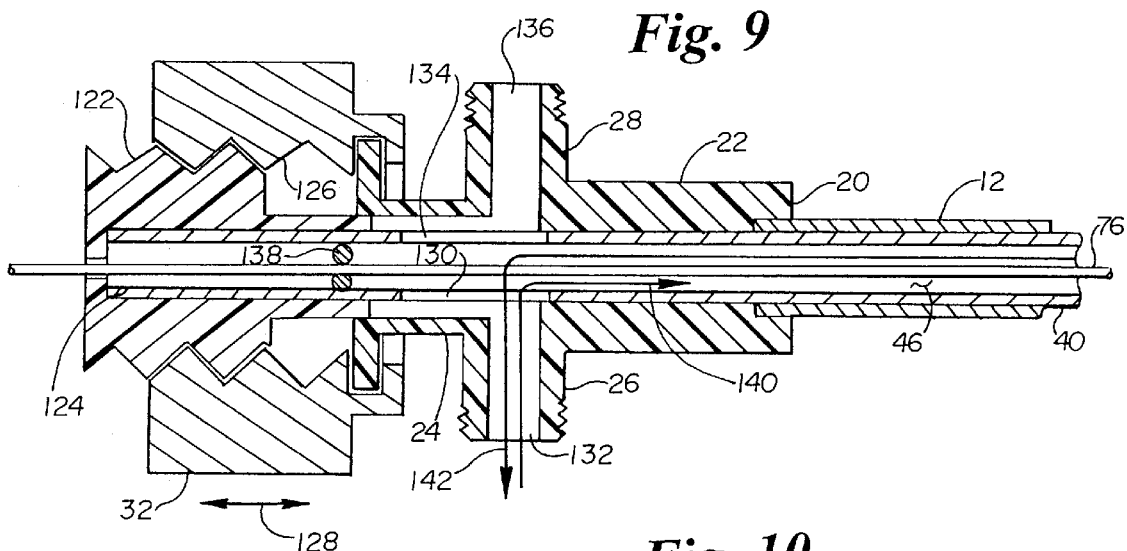
FIG. 9 is a section view of the exterior control mechanism positioned to inflate a positioned balloon.

FIG. 9 is section view of the exterior control mechanism positioned to inflate a positioned balloon. A manifold structure 24 has threaded pipe structures 26 and 28. Mounting structure 22 secures the proximal end 20 of outer body 12. A threaded structure 122 supports the distal end of guidewire 76 and is affixed to the distal end 124 of catheter 40. Of course, if a guidewire 76 is not used, the lumen 46 can be closed at the location of seal 138. Control knob 32 has a mating threaded portion 126 for causing threaded portion 122 and the catheter structure 40 to move backward and forward in the direction of arrow 128 depending upon the direction of rotation. Catheter 40 has elongated aperture 130 in fluid-flow communication with opening 132 and elongated aperture 134 in fluid-flow communication with opening 136. A seal 138, such as an 0-ring, seals fluid in lumen 46 from flowing outwardly through the end of threaded member 122, while allowing guidewire 76 to be axially positioned. As illustrated, tube port 132 can receive inflation medium and cause it to be directed through aperture 130 into lumen 46 in the direction of arrow 140 to inflate the balloon structure 14 as described above. During insertion of inflation medium, port 136 is blocked. During deflation of the balloon structure, inflation medium will be drawn back through lumen 46, and through the elongated aperture 130 through port 132 in the direction of arrow 142.

Figure 10:
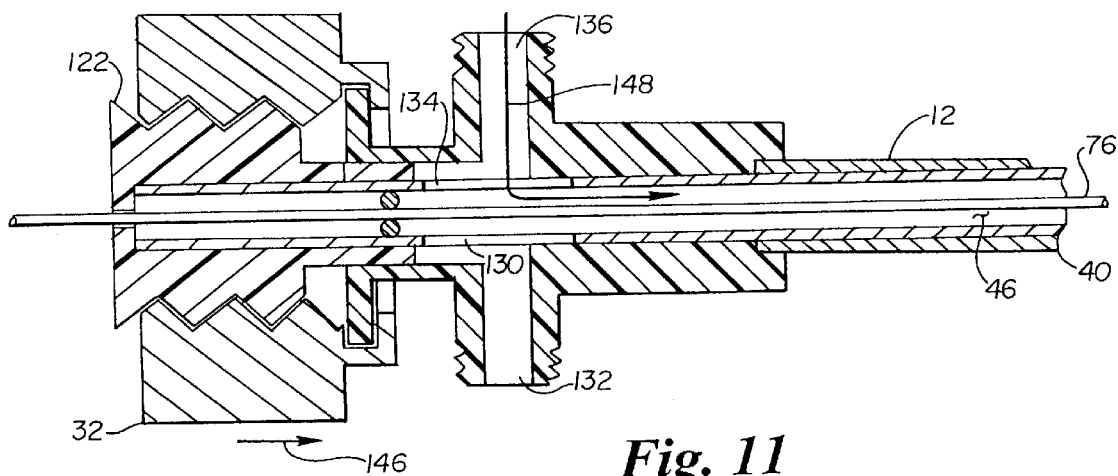
FIG. 10 is a section view of the exterior control mechanism positioned to distally perfuse the vascular lumen when the positioned balloon is inflated.

FIG. 10 is a section view of the exterior control mechanism positioned to distally perfuse the vascular lumen when the positioned balloon is inflated. As illustrated, the control 32 has been rotated to cause the threaded positioning member 122 to be moved sufficiently in the direction of arrow 146 to cause the distally positioned apertures described with respect to FIG. 5 to be aligned. Elongated apertures 130 and 134 are moved along with the movement of catheter 40, but remain in fluid-flow relationship with respect to ports 132 and 136 respectively. When thus positioned, perfusion medium can be inserted through port 136 and through aperture 134 into lumen 146 to pass in the direction of arrow 148. During insertion of perfusion medium, port 132 is blocked.

Figure 11:
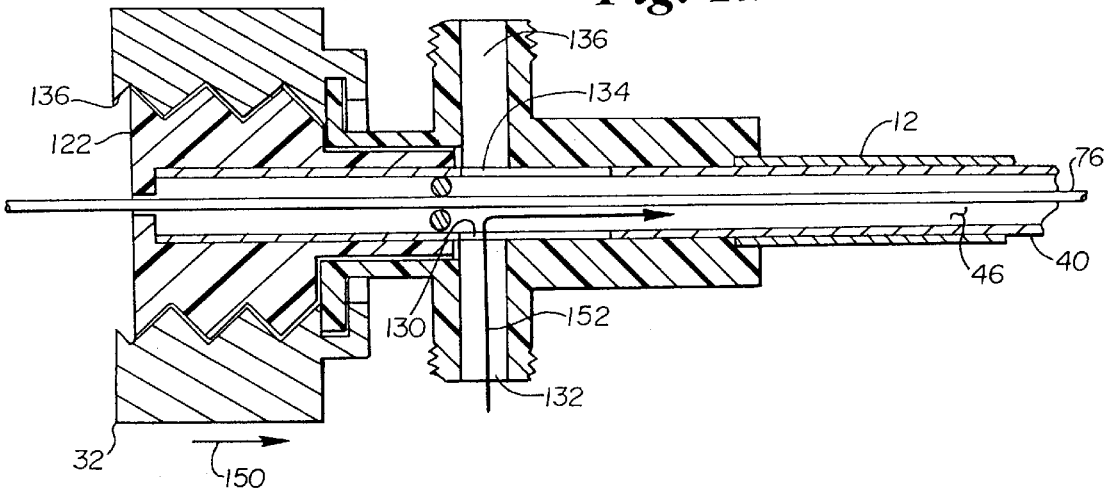
FIG. 11 is a section view of the exterior control mechanism positioned to retrograde perfuse the vascular lumen at the proximal end of the inflated balloon.

FIG. 11 is a section view of the exterior control mechanism positioned to retrograde perfuse the vascular lumen at the proximal end of the inflated balloon. In this configuration, control 32 has been rotated sufficiently to cause its threaded members 136 to move the threaded positioning member 132 a distance in the direction of arrow 150 that is sufficient to cause the mating apertures utilized for retrograde perfusion, as described with regard to FIG. 7, to be aligned. When properly positioned, retrograde perfusion medium can be inserted through port 132 and cause to flow through aperture 130 into lumen 46 of catheter 40, in the direction of arrow 152. When retrograde perfusion medium is thus inserted, port 136 is blocked.

When the total medical procedure has been completed, and it is desired to remove the catheter structure 10 completely, it is necessary to deflate balloon structure 14. Referring back to FIG. 9, this is accomplished by moving the control 32 in such a manner that the cooperating threaded control structure 122 is moved back to an original position such that the inflation/deflation mating apertures described with regard to FIG. 3 are back in alignment. As indicated, the inflation medium can be drawn off in the direction of arrow 142 through port 132.

Materials utilized to construct the improved catheter structure 10 are those known in the art. If a separate guidewire 76 is utilized, it will characteristically be constructed of stainless steel wire. In some uses, the tip or coiled tip 18 will be constructed of stainless steel or other suitable radiopaque materials. In the event that a guidewire 76 running the entire length of the multi-function catheter system is not used, and the elongated catheter portion itself is steerable, it is anticipated that the guiding portion would be a length of guidewire or hypotube extending within lumen 46 of catheter 40 from a position proximal of the mounting of the inflatable balloon structure, and extending outwardly through end member 78 of the catheter and end member 70 of the outer body member. It is contemplated that this foreshortened device could be constructed of stainless steel hypotube and similarly can have the flexible helical spring member at the distal end thereof. It is intended that the multi-function catheter structure be able to be utilized in relatively small vascular and coronary arteries. It is of course understood that the inflatable circumference of inflatable balloon structure will be selected to accommodate the size of the lumen to be treated. The elongated outer body 12 and the elongated catheter 40 can be fashioned from the required lengths of stainless steel hypotube material that are selected with an outside diameter of the catheter portion 40 to slidably engage the inner surface of the outer body 12. The outside diameter of the elongated outer body tubing would characteristically not exceed 0.020 inch and may have an outside diameter of 0.014 inch or less.

It is anticipated that the inflation medium will be a suitable saline solution. The antegrade perfusion fluid will be inserted in the vascular lumen distal of the inflated balloon structure 14, and will characteristically be accomplished by active perfusion of autologous blood. The retrograde perfusion medium will be a suitable saline solution and will be inserted proximally of the inflated balloon structure 14 to allow collection of embolus in an associated collection catheter as will be described below.

Figure 12:
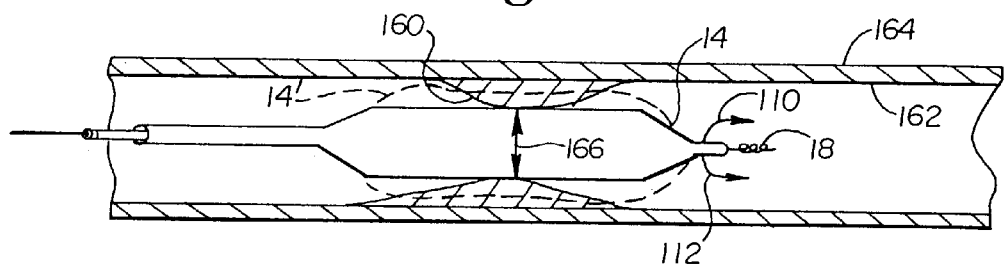
FIG. 12 illustrates use of the multi-function catheter to compress stenosis of an artery.

FIG. 12 illustrates use of the multi-function catheter to compress stenosis of an artery. In this configuration, a compression form of angioplasty is contemplated, with the inflatable balloon structure 14 being positioned in proximity to the stenosis 160. Inflation medium can then be inserted thereby causing outward pressure in the direction of the surface of balloon 14 in the direction of arrow 166 to cause compression of the stenosis. When sufficiently inflated, the inflatable balloon structure 14 will closely approximate the normal interior circumference 162 of vascular or coronary lumen 164. As is known, holding the inflatable balloon structure 14 inflated, as shown by dashed lines 14-1, for a period of time will tend to cause the stenosis to be compressed in a manner to allow dilatation of the artery 164 being treated. During the time of such compression, antegrade perfusion occurs as shown at arrows 110 and 112 and as described with regard to FIG. 5. The antegrade perfusion distally of the inflated balloon structure 14-1 allows the compression to remain in place for sufficient time to work the desired compression of the stenosis without causing downstream damage to the artery or the heart.

Figure 13:
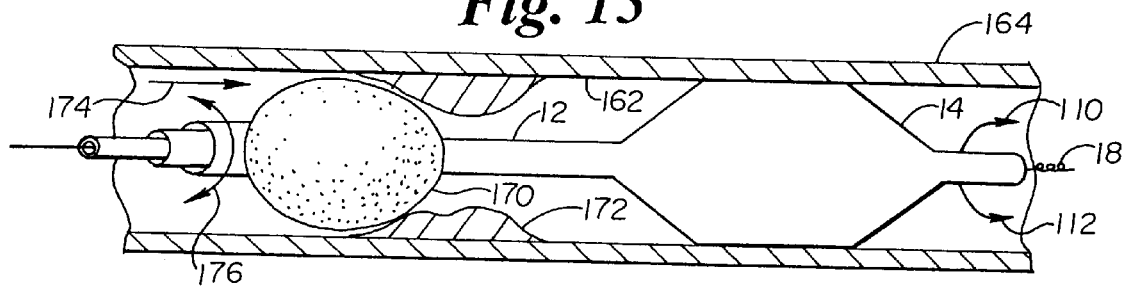
FIG. 13 illustrates use of the multi-function catheter in conjunction with a shaped abrasive device for grinding down stenosis of an artery.

FIG. 13 illustrates of the multi-function catheter in conjunction with a shaped abrasion device for grinding down stenosis of an artery. In this configuration, once the inflatable balloon structure 14 is inflated as previously described to contact the inner surface 162 of artery 164, and the distal perfusion has been instituted, a shaped abrasive device 170 is moved along elongated outer body 12 to a point such that its leading surfaces come into contact with the stenosis 172 by insertion in the direction of arrow 174. When thus in contact, external power is applied to rotate the shaped device 170 either clockwise or counterclockwise as indicated by arrow 176. As the shaped device 170 is rotated, it is continually urged in the direction of arrow 174 until the stenosis 172 has been abraded away. Such abrasion causes formation of embolus that must be dealt with to avoid further damage to the vascular system. It is understood that the largest diameter of abrasive device 170 will approximate the interior circumference of artery 164, and will thus require that the appropriate size and shaped abrasive device be selected for the artery to be treated. Once the abrasive device 170 has moved past the area of stenosis, it can be withdrawn along elongated outer member 12 to allow further treatment, and removal of the embolus.

Figure 14:
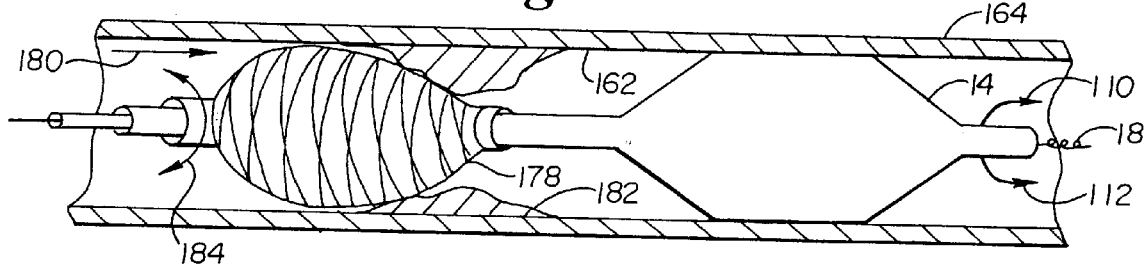
FIG. 14 illustrates use of the multi-function catheter in conjunction with an expandable cutting mechanism for cutting down stenosis of an artery.

FIG. 14 illustrates use of the multi-function catheter in conjunction with an expandable cutting mechanism for cutting down stenosis of an artery. In this configuration, an expandable cutting structure 178, comprised of a plurality of inter-related, flexible cutting members, is positioned in the direction of arrow 180 to a point where its leading cutting elements engage stenosis 182 within artery 164. When thus positioned, following insertion and inflation of inflatable balloon member 14, external power can be applied to cause rotation clockwise or counterclockwise as indicated by arrow 184 to thereby apply a cutting action to stenosis 182. Further urging in the direction of arrow 180 will cause the stenosis 180 to be cut down to a point approximating the interior circumference of artery 164. Since the expandable cutting member 178 varies in its maximum circumference of cutting, it can start with a stenosis that is rather severe such that the expandable cutting element 178 is compressed and continue to cut away and expand as the stenotic material is removed. Again, once the stenotic material has been reduced to embolus, the expandable cutting element can be withdrawn and the embolus can be dealt with.

Figure 15:
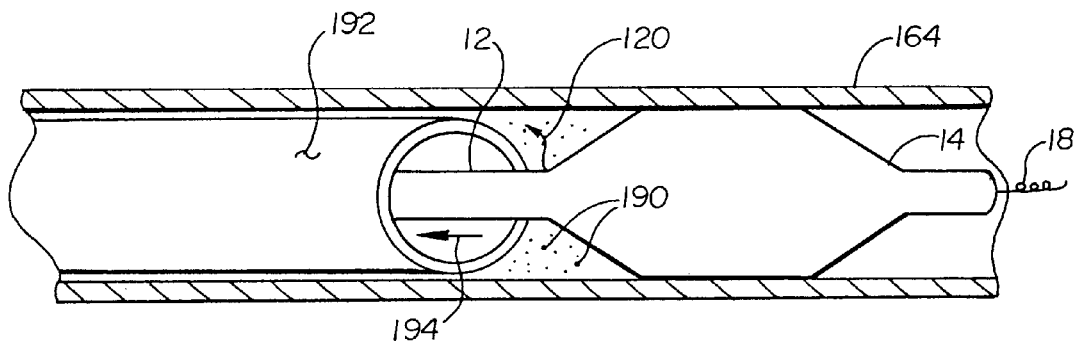
FIG. 15 illustrates an arrangement for drawing off embolus using retrograde perfusion at the proximal end of an inflated balloon that is occluding the lumen of an artery.

FIG. 15 illustrates an arrangement for drawing off embolus using retrograde perfusion at the proximal end of an inflated balloon that occluding the lumen of an artery. As previously described, the removal the stenosis often results in the generation of stenotic material being reduced to embolus 190 in the bloodstream proximally of the inflated balloon structure that occluding artery 164. Once the stenosis abrading devices are removed, a guide catheter 192 is inserted along the elongated outer body 12 to a position in relative close proximity to the proximal end of the inflated balloon structure 14. As indicated above, the multi-function catheter can be positioned such that the retrograde perfusion occurs when the retrograde apertures are appropriately aligned and retrograde perfusion medium is injected into the arterial lumen as indicated by arrow 120. The proximal end of guide catheter can then have a vacuum applied thereto such that the retrograde perfusion medium and the embolus are withdrawn in the direction of arrow 194. This removal of embolus protects the arterial system from further damage once the inflated balloon structure 14 deflated and the multi-function catheter is removed.

FIG. 16 is a block diagram of the controls utilized to operate the multi-function catheter and balloon structure to perform the functions of occluding the artery, providing distal perfusion past the inflated balloon and providing retrograde perfusion at the proximal end of the inflated balloon. A function selector 200 will control the inflation of balloon structure 14, control the antegrade perfusion, and control the retrograde perfusion for the treatment functions. It will additionally control the deflation of the balloon structure 14, all as described with regard to FIGS. 9, 10, and ii. The multi-function catheter is percutaneously inserted in artery 164. Inflation medium is provided in container 202 and is provided by pump 204 through valve 206 into port 132. For inflation, the inflation/deflation control 208 will cause pump 204 to move the inflation medium into port 132 and into catheter lumen 46. For deflation, the function selector is moved to the deflation position and the inflation/deflation control 208 causes pump 204 to reverse its action and to draw the inflation medium out through port 32 and valve 206. Once inflation is completed, valve 206 is closed. During inflation, valves 210 and 212 are closed.

Once the function selector 200 has been adjusted to select a perfusion, valve 210 is opened and valve 206 and 212 are closed. A control 214 causes pump 216 to provide perfusion medium from a source 218. The perfusion medium passes through valve 210 into catheter lumen 46 for providing the antegrade perfusion distally of the inflated balloon structure. Once perfusion is under way, the stenosis can be treated as described above. The insertion, control, and removal of the treating structures are as described with regard to FIGS. 12, 13 or 14 and are not illustrated here. Once the treating structures are removed, the guide catheter 192 is inserted to the proximal vicinity of inflated balloon structure 14. To cause the removal of embolus 190, a retrograde perfusion medium is applied from source 220 by pump 222. The control 224 determines the rate and pressure of the retrograde perfusion medium. During retrograde perfusion, valve 206 and valve 210 are closed such that the retrograde perfusion medium passes through port 132 into catheter lumen 46 and out into the arterial lumen as indicated by arrow 120. Once the retrograde perfusion is started, the embolus removal control 226 causes the vacuum device 228 to draw off embolus and retrograde perfusion medium through valve 230 and to put it in discharge container 232. The removal process continues for a relatively short time in that the distally administered medium is cut off during the time of embolus removal.

Upon completion of removal of the embolus, the guide catheter 192 is removed, valve 230 is closed, pump 222 is turned off and valve 212 is closed. At that time, the deflation procedure is implemented as described. Upon deflation and the establishment of normal blood flow, the multi-function guide catheter is removed. The pumps 204, 206 and 222 may be any mechanism that is capable of providing the requisite pressure to its associated medium, and valves 206, 210 and 212 can be any structure that will pass or block the medium in its associated line. The controls 208, 214 and 226 can be manual or integrated automotive systems adapted to control their respective functions.

Figure 17:
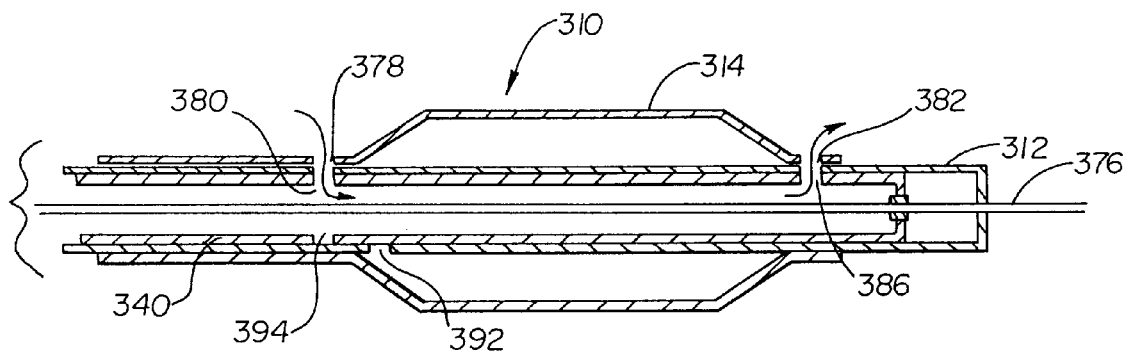
FIG. 17 is a longitudinal, cross-sectional view of the distal end of an alternative embodiment of the multi-functional catheter in accordance with the present invention.

In an alternate embodiment of the present invention, an arrangement of apertures can be provided for active perfusion. FIG. 17 is a longitudinal cross sectional view of the distal end of a multi-functional catheter 310 in accordance with the present invention. Catheter 310 includes an outer body member 312 and an elongate catheter 340 extending over guidewire 376. Elongate catheter 340 is shiftable coaxially and longitudinally within outer body member 312 such that apertures 392 and 394 may be aligned to deliver inflation fluid to a balloon 314 by way of a longitudinal lumen extending through catheter 340. Alternately, as shown in FIG. 17, catheter 340 may be aligned such that apertures 378 and 380 and apertures 382 and 386, respectively, are aligned for active perfusion. As shown by the arrows in FIG. 17, blood or another fluid can enter apertures 378 and 380, travel through a lumen extending longitudinally through catheter 340 and exit through apertures 382 and 386. A reverse flow pattern is also possible depending upon the location in which catheter 310 is used. The manufacture and use of catheter 310 is substantially similar to that of catheter 10 described above, however, active perfusion is provided for.

From the foregoing, it can seen that the various purposes and objectives of the invention have been achieved. It is understood that various modifications, will become apparent to those skilled in the art without departing from the spirit and scope of the invention. What is intended to be protected by Letters Patent is set forth in the appended claims.

What is claimed is:

1. For use in percutaneously positioning in a stenotic region of an artery and treatment of the stenosis, a multi-function catheter comprising:

an elongated catheter body having an outer surface, a proximal end, a distal end and an inner lumen, said catheter body having at least a first perfusion aperture at a position near said distal end, and a first inflation aperture proximally spaced a first distance from said first perfusion aperture;

an elongated outer body coaxially positioned along said elongated catheter body and having an inner lumen with an inner surface slidably engaging said outer surface, said elongated outer body having a second perfusion aperture positioned for fluid-flow cooperation with said first perfusion aperture when said elongated outer body is in a first relative position with said elongated catheter body, and a second inflation aperture proximately spaced a second distance from said second perfusion aperture, said second distance being different than said first distance, said second inflation aperture positioned for fluid-flow cooperation with said first inflation aperture when said elongated outer body is in a second relative position with said elongated catheter body; and an inflatable balloon structure having a proximal end sealed proximally of said second inflation aperture and having a distal end sealed proximally of said first perfusion aperture and said second perfusion aperture, whereby inflation fluid can be applied through said lumen of said elongated catheter body to inflate said inflatable balloon structure when said first inflation aperture is positioned in fluid-flow cooperation alignment with said second inflation aperture and whereby perfusion fluid can be applied through said lumen to perfuse fluid distally of said inflatable balloon structure when said first perfusion aperture is positioned in fluid-flow cooperation alignment with said second perfusion aperture.

2. A multi-function catheter as in claim 1 and further including:

a first retrograde perfusion aperture in said elongated catheter body positioned proximally of said inflated balloon structure; and a second retrograde perfusion aperture in said elongated outer body positioned for fluid-flow cooperation with said first retrograde perfusion aperture when said elongated outer catheter body is in a third relative position with said elongated outer body.

3. A multi-function catheter as in claim 1, wherein said second distance is greater than said first distance.

4. A multi-function catheter as in claim 3, wherein said first perfusion aperture and said second perfusion aperture each further include a similar plurality of perfusion apertures arranged for fluid-flow cooperation therethrough when aligned in said first relative position.

5. A multi-function catheter as in claim 3, wherein said first inflation aperture and said second inflation aperture each further include a similar plurality of inflation apertures arranged for fluid-flow cooperation therethrough when aligned in said second position.

6. A multi-function catheter as in claim 2, wherein said first retrograde perfusion aperture and said second retrograde perfusion aperture each further include a similar plurality of retrograde perfusion apertures arranged for fluid-flow cooperation therethrough when aligned in said third position.

7. A multi-function catheter as in claim 1, and further including:

a control mechanism coupled to the proximal end of said elongated catheter body and coupled to said elongated outer body to selectively move said elongated catheter body to said first position or said second position.

8. A multi-function catheter as in claim 7, and further including:

a manifold coupled to said elongated catheter body for selectively applying inflation fluid or perfusion fluid in said lumen.

9. A multi-function catheter as in claim 2, and further including:

a control mechanism coupled to the proximal end of said elongated catheter body and coupled to said elongated outer body to selectively move said elongated catheter body to said first position, said second position, or said third position.

10. A multi-function catheter as in claim 9, and further including:

a manifold coupled to said elongated catheter body for selectively applying inflation fluid, perfusion, or retrograde perfusion fluid, in said lumen.

11. For use in percutaneous positioning in a stenotic region of an artery and treatment of the stenosis, a multi-function catheter comprising:

catheter means having a first plurality of apertures, a proximal end, a distal end, and a longitudinal lumen, said catheter means for carrying selected fluids;

outer body means for slidably encasing said catheter means, said outer body means having a distal end, a proximal end, and a second plurality of apertures;

inflatable occlusion means mounted on said outer body means for occluding a vascular lumen when inflated;

inflation means for passing inflation fluid through said lumen to inflate said inflatable occlusion means when first selected ones of said first and said second plurality of apertures are in a first relative fluid-flow position; and perfusion means for passing perfusion fluid through said lumen to provide said perfusion fluid distally of said inflatable balloon means when second selected ones of said first and second plurality of apertures are in a second relative fluid-flow position.

12. A multi-function catheter as in claim 11, and further including:

retrograde perfusion means for passing retrograde perfusion fluid through said lumen to provide said retrograde perfusion fluid proximally of said inflatable occlusion means when third selected ones of said first and second plurality of apertures are in a third relative fluid-flow position.

13. A multi-function catheter as in claim 12, and further including:

stenosis removal means for removing stenotic material.

14. A multi-function catheter as in claim 13, wherein said stenosis means includes embolus means for causing stenotic material to be reduced to embolus.

15. A multi-function catheter as in claim 14, and further including:

embolus removal means for removing embolus suspended in said retrograde perfusion fluid.

16. A multi-function catheter as in claim 12, and further including control means coupled to said catheter means and to said outer body means for selecting said first position, said second position, or said third position.

17. A multi-function catheter comprising:

an elongated catheter having a first outer surface, a proximal end, a distal end and an inner lumen, said elongated catheter including a first plurality of spaced-apart apertures in proximity to its distal end;

an elongated outer body coaxially positioned along said elongated catheter and having a second outer surface and an inner surface in slidable contact with said first outer surface, said elongated outer body having a second plurality of spaced-apart apertures, wherein selected ones of said first plurality of spaced-apart apertures are arranged to cooperate with like selected ones of said plurality of spaced-apart apertures to provide selectable fluid-flow positioned from said inner lumen through said elongated outer body; and an inflatable balloon structure having a proximal end and distal end sealed to said second outer surface.

18. A multi-function catheter as in claim 17, wherein said selected ones of said first plurality of spaced-apart apertures and selected ones of said second plurality of spaced-apart apertures are a predetermined set of groups of apertures.

19. A multi-function catheter as in claim 18, wherein only one of said groups of apertures in said set are in said fluid-flow position while the others of said groups of apertures in said set are not in said fluid-flow position.

20. A multi-function catheter as in claim 19, wherein said inner lumen is adapted to selectively convey inflation fluid, antegrade perfusion fluid, and retrograde perfusion fluid.

21. A multi-function catheter as in claim 20, wherein said groups of apertures in said set include an inflation fluid group and a perfusion fluid group.

22. A multi-function catheter as in claim 21, wherein said groups of apertures in said set further includes a retrograde perfusion fluid group.

23. A multi-function catheter as in claim 21, and further including:

a control mechanism coupled to said elongated catheter and to said elongated outer body to selectively adjust the longitudinal relationship of said elongated catheter with respect to said elongated outer body to select which of said groups of apertures in said set will be in fluid-flow position with said inner lumen.

24. A multi-function catheter as in claim 23, wherein said control mechanism selects said inflation fluid group to pass inflation fluid from said inner lumen to inflate said inflatable balloon structure.

25. A multi-function catheter as in claim 24, wherein said control mechanisms selects said perfusion fluid group to pass perfusion fluid from said inner lumen distally from inflatable balloon structure.

26. A multi-function catheter as in claim 25, wherein said group of apertures in said set further includes a retrograde perfusion group, and said control mechanism selects said retrograde perfusion group to pass retrograde perfusion fluid from said inner lumen proximally from said inflatable balloon structure.

27. A multi-function catheter as in claim 26, and further including:

a stenosis removal device supported by said elongated outer body to reduce stenotic material to embolus.

28. A multi-function catheter as in claim 27, and further including:

an embolus retrieval system to cooperate with said retrograde perfusion group to withdraw said embolus and said retrograde perfusion fluid from the artery.

29. The method of removing stenosis from an artery utilizing a multi-functional, percutaneously inserted catheter having an elongated catheter with an inner lumen, an elongated outer body coaxially aligned and in slidable contact with the elongated catheter, an inflatable balloon to occlude the artery, the elongated catheter and the elongated outer body having a plurality of spaced-apart apertures arranged to form a set of inflation apertures, a set of perfusion apertures and a set of retrograde perfusion apertures, the method comprising:

aligning the set of inflation apertures and applying inflation fluid to the inflatable balloon from the inner lumen through the set of inflation apertures;

aligning the set of perfusion apertures and applying perfusion fluid from the inner lumen through the set of perfusion apertures to the artery lumen distally from the inflated balloon;

removing the stenotic material; and aligning the set of retrograde perfusion apertures and applying retrograde perfusion fluid from the inner lumen to the artery lumen proximally from the inflated balloon.

30. The method of claim 29, wherein the step of removing stenotic material includes the formation of embolus; and removing the embolus and the retrograde perfusion fluid from the artery.

* * * * *